(12) United States Patent
Mukae et al.

(10) Patent No.: US 12,741,924 B2
(45) Date of Patent: Sep. 22, 2026

(54) PURIFICATION DEVICE

(71) Applicant: NIPPON SHOKUBAI CO., LTD., Osaka (JP)

(72) Inventors: Masashi Mukae, Himeji (JP); Yasutaka Takemoto, Himeji (JP); Hiroki Wada, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 716 days.

(21) Appl. No.: 18/025,606

(22) PCT Filed: Sep. 8, 2021

(86) PCT No.: PCT/JP2021/033034
§ 371 (c)(1),
(2) Date: Mar. 9, 2023

(87) PCT Pub. No.: WO2022/054840
PCT Pub. Date: Mar. 17, 2022

(65) Prior Publication Data

US 2023/0373897 A1 Nov. 23, 2023

(30) Foreign Application Priority Data

Sep. 11, 2020 (JP) ................................ 2020-153286
Jan. 7, 2021 (JP) ................................ 2021-001398

(51) Int. Cl.
*C07C 51/47* (2006.01)
*B01D 35/027* (2006.01)
*C07C 51/43* (2006.01)

(52) U.S. Cl.
CPC ............ *C07C 51/47* (2013.01); *B01D 35/027* (2013.01); *C07C 51/43* (2013.01)

(58) Field of Classification Search
CPC ........ C07C 51/47; C07C 51/43; B01D 35/027
See application file for complete search history.

(56) References Cited

U.S. PATENT DOCUMENTS 7,112,695 B2 9/2006 Eck et al.
2003/0060661 A1 3/2003 Eck et al.
(Continued)

FOREIGN PATENT DOCUMENTS

CN 102471214 A 5/2012
CN 102666464 A 9/2012
(Continued)

OTHER PUBLICATIONS

P. J. Jansens, et al., The Purification Process in Hydraulic Packed-Bed Wash Columns, Chemical Engineering Science, vol. 50. No. 17, pp. 2717-2729, 1995, Delft University of Technology, The Netherlands, and Tokyo University of Agriculture and Technology, Japan, Copyright © 1995 Elsevier Science Ltd.
(Continued)

*Primary Examiner* — Amy C Bonaparte
*Assistant Examiner* — Derek Rhoades
(74) *Attorney, Agent, or Firm* — Dickinson Wright PLLC

(57) ABSTRACT

The present invention provides a method for obtaining high-quality products. The present invention relates to a purification apparatus that purifies crystals, the purification apparatus including: a hydraulic wash column that includes a discharging port for a crystal-containing circulation slurry and a return port for a circulation liquid containing a melt of discharged crystals; a pipe that feeds a crystal-containing slurry to the hydraulic wash column; a filter that filters the crystal-containing slurry in the hydraulic wash column; a pipe that is connected to the filter and discharges a mother liquor; and a unit that melts crystals in a circulation slurry discharged through the discharging port, wherein a distance between a lower end of the filter and an average bottom surface level of the hydraulic wash column is 1000 mm or more.

19 Claims, 2 Drawing Sheets

(56) References Cited

U.S. PATENT DOCUMENTS

| | | | | |
|---|---|---|---|---|
| 2003/0175159 | A1 | 9/2003 | Heilek et al. | |
| 2004/0049077 | A1 | 3/2004 | Eck et al. | |
| 2004/0256319 | A1 | 12/2004 | Hammon et al. | |
| 2005/0006299 | A1 | 1/2005 | Heilek et al. | |
| 2005/0252557 | A1* | 11/2005 | Kabu et al. | F17D 1/00 137/599.01 |
| 2006/0237356 | A1 | 10/2006 | Heilek et al. | |
| 2007/0129572 | A1 | 6/2007 | Shibusawa et al. | |
| 2010/0206821 | A1 | 8/2010 | Helek et al. | |
| 2011/0124834 | A1 | 5/2011 | Heilek et al. | |
| 2012/0108857 | A1 | 5/2012 | Sakamoto et al. | |

FOREIGN PATENT DOCUMENTS

| | | | |
|---|---|---|---|
| CN | 102755763 | A | 10/2012 |
| DE | 100 17 903 | A1 | 10/2001 |
| EP | 1272453 | B1 | 11/2005 |
| JP | 2003-530376 | A | 10/2003 |
| JP | 2005-509009 | A | 4/2005 |
| JP | 2007-182437 | A | 7/2007 |
| JP | 2008-536893 | A | 9/2008 |
| JP | 2010-059107 | A | 3/2010 |
| JP | 2012-518023 | A | 8/2012 |
| JP | 2013-507427 | A | 3/2013 |

OTHER PUBLICATIONS

International Search Report dated Nov. 2, 2021, which issued in the corresponding PCT Patent Application No. PCT/JP2021/033034.

* cited by examiner

PURIFICATION DEVICE

TECHNICAL FIELD

The present invention relates to purification apparatuses. More specifically, the present invention relates to a purification apparatus, a method for producing a compound, and a method for purifying a compound.

BACKGROUND ART

Purification apparatuses are widely used industrially to purify easily polymerizable compounds such as (meth) acrylic acid, which are used as raw materials for resins, for example. Various studies have been made on better purification apparatuses for obtaining high-quality compounds with reduced impurities.

Industrially, many of crude compounds, which are compounds before purification, are purified through continuous purification processes. Disclosed is a method for producing acrylic acid including: collecting and crystallization purifying a gas containing acrylic acid obtained by catalytic oxidation of a raw material gas in gas phase; and returning acrylic acid obtained by decomposing a substance obtained by Michael addition of acrylic acid in a residual mother liquor to the collecting step, for example (see, for example, Patent Literature 1).

In the purification process, a wash column such as a hydraulic wash column (HWC) may be used as a solid-liquid separation apparatus. Patent Literatures 2 to 5 disclose purification methods and the like using conventional wash columns. These wash columns contain filter tubes for filtering the slurry in the wash columns and discharging and recovering the mother liquor.

CITATION LIST

Patent Literature

Patent Literature 1: JP 2007-182437 A
Patent Literature 2: JP 2013-507427 T
Patent Literature 3: JP 2012-518023 T
Patent Literature 4: JP 2008-536893 T
Patent Literature 5: JP 2003-530376 T

SUMMARY OF INVENTION

Technical Problem

As described above, better purification apparatuses for producing compounds have been desired to obtain high-quality products (compounds). The present invention has been made in view of the above-mentioned current state of the art, and aims to provide a method for obtaining high-quality products.

Solution to Problem

The present inventors have studied purification apparatuses and focused on a hydraulic wash column with high washing efficiency, and found the following. In a hydraulic wash column in which the distance between the lower end of the filter that filters a crystal-containing slurry and an average bottom surface level of the hydraulic wash column is 1000 mm or more, impurities, particularly solid solution impurities such as acetic acid and propionic acid when acrylic acid is a target compound, melt and resolidify at the lower end of the filter, and thus can be separated with higher efficiency, leading to production of high-quality products. Thereby, the present invention has been achieved.

That is, the present invention relates to a purification apparatus that purifies crystals, the purification apparatus including: a hydraulic wash column that includes a discharging port for a crystal-containing circulation slurry and a return port for a circulation liquid containing a melt of discharged crystals; a pipe that feeds a crystal-containing slurry to the hydraulic wash column; a filter that filters the crystal-containing slurry in the hydraulic wash column; a pipe that is connected to the filter and discharges a mother liquor; and a unit that melts crystals in a circulation slurry discharged through the discharging port, wherein a distance between a lower end of the filter and an average bottom surface level of the hydraulic wash column is 1000 mm or more.

Patent Literatures 2 to 4 disclose the length of a filter tube displacer arranged from the lower end of the filter to the bottom surface of the wash column, and the length was 500 mm at most, which was very short.

Advantageous Effects of Invention

The purification apparatus of the present invention can provide a high-quality product.

DESCRIPTION OF EMBODIMENTS

Figure 1:
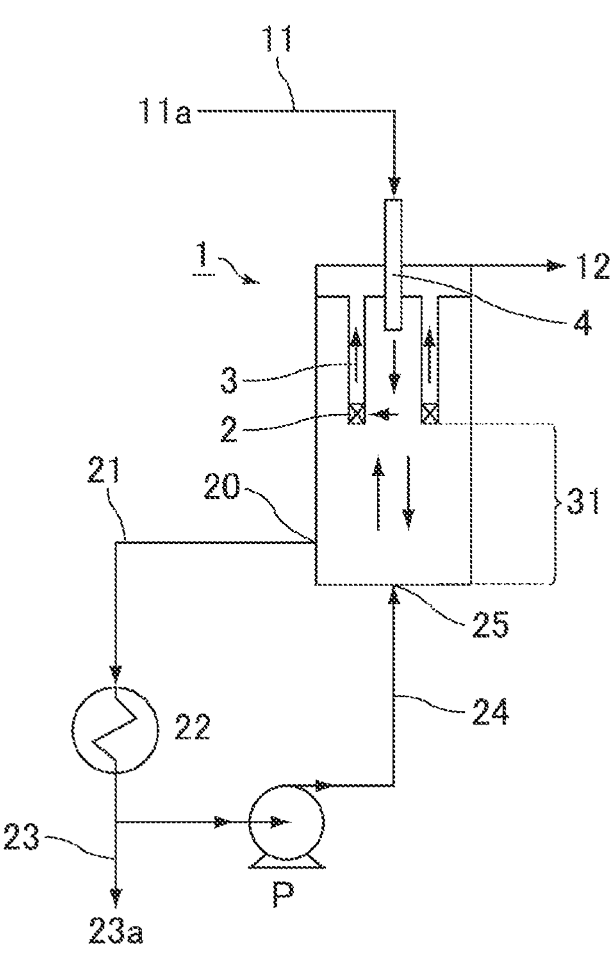
FIG. 1 is an exemplary schematic diagram of the state of use of the purification apparatus of the present invention.

The present invention will be described in detail below.

It should be noted that combinations of two or more of the preferred features of the present invention described below are also preferred embodiments of the present invention.

The following first describes a purification apparatus of the present invention, followed by descriptions of a method for producing a compound of the present invention and a method for purifying a compound of the present invention in this order.

(Purification Apparatus of the Present Invention)

The purification apparatus of the present invention includes a hydraulic wash column that includes a discharging port for a crystal-containing circulation slurry and a return port for a circulation liquid containing a melt of discharged crystals; a pipe that feeds a crystal-containing slurry to the hydraulic wash column; a filter that filters the crystal-containing slurry in the hydraulic wash column; a pipe that is connected to the filter and discharges a mother liquor; and a unit that melts crystals in a circulation slurry discharged through the discharging port, wherein a distance between a lower end of the filter and an average bottom surface level of the hydraulic wash column is 1000 mm or more.

As for the purification apparatus of the present invention, in the hydraulic wash column in which the distance between the lower end of the filter and the average bottom surface level of the hydraulic wash column is 1000 mm or more, the space velocity of the crystal bed below the filter is appropriately reduced. In other words, it is considered that the residence time of the crystal bed below the filter is sufficiently long, leading to excellent impurity separation efficiency.

The distance is preferably 1500 mm or more, more preferably 2000 mm or more.

In the purification apparatus of the present invention, the distance between the lower end of the filter and the average bottom surface level of the hydraulic wash column is not limited as long as it is 1000 mm or more. Considering the apparatus scale and efficiency, the distance is preferably 10000 mm or less. The distance is more preferably 8000 mm or less, still more preferably 7000 mm or less, particularly preferably 6000 mm or less.

The average bottom surface level of the hydraulic wash column refers to the average entire bottom surface level of the hydraulic wash column during use.

In the case of a hydraulic wash column in which multiple filters are present, the distance between the lower end of the filter and the average bottom surface level of the hydraulic wash column may correspond to the distance between the lower end of any one of the filters and the average bottom surface level of the hydraulic wash column, preferably corresponds to the distance between the lowest one among the lower ends of the filters and the average bottom surface level of the hydraulic wash column.

The pipe that is connected to the filter and discharges a mother liquor is usually located above the filter. The discharged mother liquor can be recycled. Thereby, the compound can be produced in improved yield. For example, the discharged mother liquor can be used as a portion of the crystal-containing slurry to be fed to the hydraulic wash column.

The filter may be made of any material and may be made of, for example, metal such as stainless steel or resin such as polytetrafluoroethylene (PTFE) or polyetheretherketone (PEEK), with the latter being preferred. The pipe may be made of any material and may be made of metal or an alloy, for example.

The purification apparatus of the present invention may further include a dummy pipe that is connected to the filter that filters the crystal-containing slurry in the hydraulic wash column.

The dummy pipe is usually located below the filter. The dummy pipe may be made of any material. For example, it is preferably made of resin such as polytetrafluoroethylene (PTFE), polyetheretherketone (PEEK), or a perfluoroalkoxy alkane (PFA).

The presence of the dummy pipe eliminates a portion where crystals are less likely to accumulate under the filter, resulting in formation of a uniform and solid crystal bed.

The dummy pipe may have any appropriate length. The length is preferably 1000 mm or longer, more preferably 1500 mm or longer, more preferably 2000 mm or longer. The length of the dummy pipe is preferably 10000 mm or shorter, considering the apparatus scale and efficiency. The length is more preferably 8000 mm or shorter, still more preferably 7000 mm or shorter, particularly preferably 6000 mm or shorter. The dummy pipe preferably extends from the lower end of the filter to the vicinity of the bottom surface of the hydraulic column.

The body or the periphery of the hydraulic wash column may be provided with instrumentation equipment such as a thermometer (e.g., a multi-point thermometer), a pressure gauge, or an interface level meter (e.g., an optical interface level meter).

The hydraulic wash column itself may be placed in a temperature-controlled casing (including a large casing such as a building).

Preferably, the purification apparatus of the present invention further includes: a discharging line that connects the discharging port for a crystal-containing circulation slurry in the hydraulic wash column and the melting unit; and a return line that connects the melting unit and the return port of the hydraulic wash column.

The discharging line is preferably installed in the vicinity of the bottom surface of the hydraulic wash column.

During use of the purification apparatus of the present invention, the circulation slurry or a circulation liquid containing a melt is circulated in the discharging line and the return line. Herein, the circulation path is also referred to as a melt loop.

In the circulation path, the circulation slurry flows a zone between a point where the circulation liquid is combined with the crystals in the hydraulic wash column to be a circulation slurry and a point where the crystals in the circulation slurry are melted. For example, in the melt loop, the circulation liquid returned through a return port 25 to the bottom of the hydraulic wash column is combined with the crystals in the hydraulic wash column to be a circulation slurry, and the circulation slurry flows in a path (a discharging line 21) between a circulation slurry discharging port 20 and a melting unit 22.

The purification apparatus of the present invention preferably includes a mechanism that discharges crystals from a crystal bed in the hydraulic wash column.

Non-limiting examples of the mechanism that discharges crystals from a crystal bed include a rotor blade or scraper described in JP 2005-509009 T and a mechanism using liquid dynamic pressure described in EP 1469926. One or more of these may be used. When the rotor blade or scraper is used, the rotation speed is preferably 20 to 60 rpm. The material of the rotor blade or scraper is preferably metal such as stainless steel.

The melting unit is usually a heater. Examples of the heater include those having a structure that efficiently transfers heat to the crystal-containing slurry, such as a vertical multitubular heat exchanger, a horizontal multitubular heat exchanger, a double pipe heat exchanger, a spiral heat exchanger, a plate heat exchanger, a corrugated tube heat exchanger, and an electric heater. Preferably, the heater is provided in the melt loop and the circulation slurry (the circulation liquid after the melting step) is circulated in the forced circulation system in which the circulation slurry is circulated by a pump provided in the melt loop.

The purification apparatus of the present invention may further include the mechanism (return mechanism) that returns a portion of the circulation liquid containing the melt obtained in the unit that melts the crystals to the hydraulic wash column.

The return mechanism may be any mechanism that is used to return a portion of the circulation liquid separated from the other portion of the circulation liquid to the hydraulic wash column. For example, when the product discharging line that is connected to a product discharging port is branched from the return line that connects the melting unit and the return port, this branched line portion corresponds to the return mechanism. For example, the branched line portion may be a T-junction.

In particular, the return mechanism preferably returns a portion of a circulation liquid containing a melt obtained in the unit that melts crystals to the hydraulic wash column so that at least a portion of the returned circulation liquid serves as a washing liquid for crystals.

The return port is preferably provided at the bottom of the hydraulic wash column so that the circulation liquid can be returned upward. The return mechanism may be, for example, a combination of the branched line portion and the return port at the bottom of the hydraulic wash column.

Preferably, the purification apparatus of the present invention further includes a product discharging port. For example, more preferably, the purification apparatus of the present invention further includes: the product discharging line branched from the return line that connects the melting unit and the return port; and the product discharging port connected to the product discharging line.

FIG. 1 shows an example of the purification apparatus of the present invention. A crystal-containing slurry 11*a* is fed into a hydraulic wash column 1 through a feed line 11 (including a pipe 4) that feeds the crystal-containing slurry to the hydraulic wash column, and the crystals deposit at the bottom of the hydraulic wash column 1 to form a crystal bed (not shown). The inside of the hydraulic wash column 1 is provided with filters 2 that filter the crystal-containing slurry in the hydraulic wash column 1 and pipes 3 that are connected to the filters and discharge a mother liquor. Thereby, a mother liquor 12 can be recovered from the crystal-containing slurry and reused.

The crystals are discharged from the bottom of the hydraulic wash column 1 together with a circulation liquid circulated in a melt loop that passes through the bottom of the hydraulic wash column 1 as a crystal-containing circulation slurry. The circulation slurry passes through the discharging line 21 that connects the circulation slurry discharging port 20 and the melting unit 22 and is sent to the unit 22 that melts the crystals in the circulation slurry. A portion of the circulation liquid containing a melt obtained by melting the crystals in the melting unit 22 is returned into the hydraulic wash column 1 through a return line 24 that connects the melting unit 22 and the return port 25. A portion of the returned circulation liquid serves as a washing liquid for crystals. The rest of the returned circulation liquid is discharged through the circulation slurry discharging port 20 together with the crystals and is recirculated in the melt loop. A portion of the circulation liquid containing the melt obtained by melting the crystals in the melting unit 22 is discharged from the purification apparatus as a purified product 23*a* through a product discharging line 23 that is branched from the return line 24 and connected to the product discharging port.

The purification apparatus of the present invention may further include the mechanism that controls the amount of the circulation liquid to be returned.

The purification apparatus of the present invention further including the mechanism that controls the amount of the circulation liquid to be returned (control mechanism) can adjust the amount of the circulation liquid to be returned, and if needed, can efficiently separate impurities. Thereby, a product can be efficiently obtained.

An example of the control mechanism is a valve installed in the line of the return mechanism (branched line portion).

The control mechanism may directly or indirectly control the amount of the circulation liquid to be returned.

When the control mechanism directly controls the amount of the circulation liquid to be returned, the control mechanism may be a valve (not shown) installed in the return line 24 shown in FIG. 1, for example.

When the control mechanism indirectly controls the amount of the circulation liquid to be returned, the control mechanism may be a valve (not shown) installed in the product discharging line 23 that is connected to the product discharging port (not shown), for example. The amount of the circulation liquid to be returned through the return line 24 can be controlled resultantly by adjusting the valve installed in the product discharging line 23.

A valve may be installed in both the product discharging line 23 and the return line 24.

Further, flowmeters may be installed in the feed line 11 (including the pipe 4) that feeds the crystal-containing slurry 11*a* to the hydraulic wash column, the product discharging line 23, and the return line 24 to measure the flow rates, and the flow rates may be appropriately adjusted by controlling the valves in accordance with the measured flow rates. Furthermore, the valves may be controlled according to the temperature in the hydraulic wash column measured with a multi-point thermometer installed therein.

Preferably, the purification apparatus of the present invention further includes a bypass line that connects the discharging line and the return line. In other words, the purification apparatus of the present invention preferably includes the discharging line that connects the discharging port and the melting unit and the return line that connects the melting unit and the return port; and further includes the bypass line that connects the discharging line and the return line.

The presence of the bypass line that connects the discharging line and the return line enables separate control of the flow rate of the circulation liquid to be returned to the hydraulic wash column and the flow rate of the circulation slurry and/or the circulation liquid to be circulated through the melting unit. This can lead to efficient operation of the entire apparatus and efficient production of a high-quality product.

When the purification apparatus of the present invention includes the bypass line, the purification apparatus may further include a distribution mechanism that controls the flow rate in the bypass line.

Examples of the distribution mechanism include valves attached to the return line and/or the bypass line. Also, a valve (such as a three-way valve) for switching the flow path may be installed in a T-junction between the return line and the bypass line. When a valve for switching the flow path is installed in a T-junction, the return line and/or the bypass line may or may not be provided with a valve or the like.

When the distribution mechanism is, for example, a valve installed in a return line portion (124*b* in FIG. 2) that connects the return port and a branch where the bypass line branches from the return line, the amount of the circulation liquid to be returned through the bypass line can be controlled resultantly by adjusting the valve.

Figure 2:
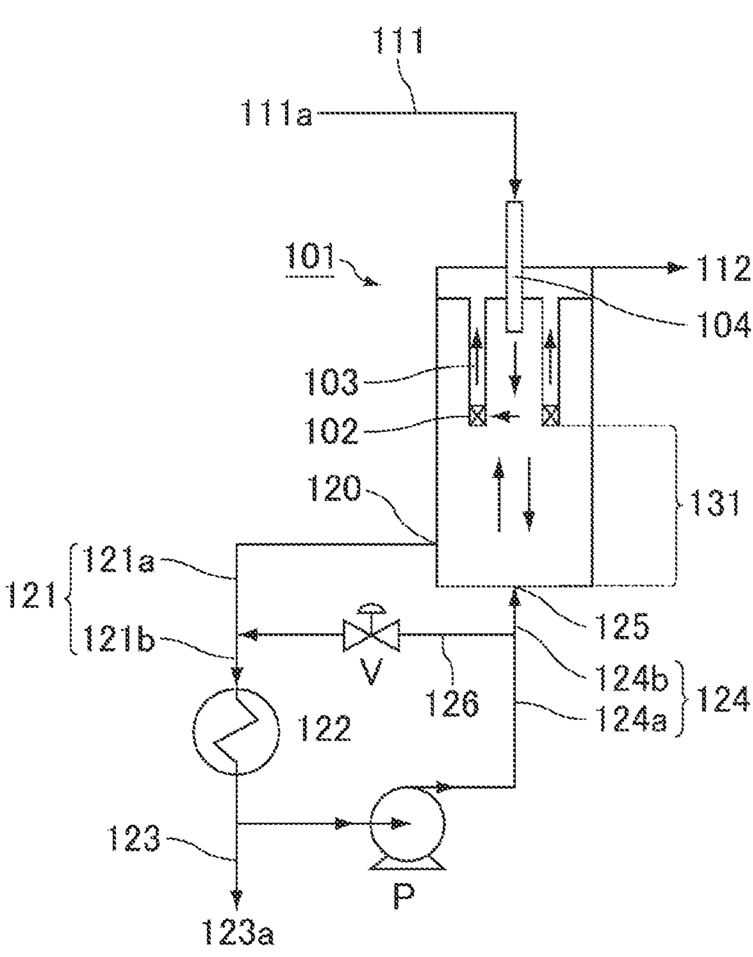
FIG. 2 is an exemplary schematic diagram of the state of use of the purification apparatus of the present invention.

When the distribution mechanism is a valve attached to the bypass line, the flow rate of the circulation liquid in the bypass line can be directly controlled. FIG. 2 illustrates the case where a valve V is attached to a bypass line 126.

The purification apparatus of the present invention may further include a unit for measuring the flow rate in each of a portion that connects the melting unit and the branch where the bypass line branches from the return line (124*a* in FIG. 2), the portion that connects the return port and the branch where the bypass line branches from the return line (124*b* in FIG. 2), and the bypass line.

The unit for measuring the flow rate is, for example, a flow meter attached to the bypass line or a predetermined point of the return line.

All the portions (124*a*, 124*b*, and 126 in FIG. 2) may be provided with a flowmeter, or the flow rates at two of the portions are measured and the flow rate of the last one portion may be calculated from these flow rates.

The discharging line, the return line, and the bypass line each may be provided with a heating mechanism. All or any of these lines may be provided with a heating mechanism.

Examples of the heating mechanism include a jacket that includes a heat retaining mechanism and uses a heating medium such as water, a steam tracing system, and an electric heater. One or more of these can be used.

The heating temperature by the heating mechanism may be appropriately selected according to the melting point of the compound, and can be appropriately adjusted within the range of 10° C. to 100° C., for example.

For example, when the compound is (meth)acrylic acid, the heating temperature by the heating mechanism is preferably 15° C. or higher, more preferably 18° C. or higher. The heating temperature is preferably 50° C. or lower, more preferably 40° C. or lower.

The heating temperature by the heating mechanism is the heating temperature in the heating mechanism. When the heating is performed by feeding a heating medium to the heating mechanism, the heating temperature is the temperature of the heating medium.

The hydraulic wash column in the purification apparatus of the present invention may have any dimensions. Preferably, the inner diameter of the column (the crystallization chamber) is 30 to 2000 mm, for example. The height of the column is preferably 1500 to 15000 mm.

The filter that filters the crystal-containing slurry in the hydraulic wash column in the present invention may have any dimensions. Preferably, the inner diameter of the filter is 10 to 30 mm, for example. The height of the filter is preferably 20 to 300 mm.

The filter may be provided with a large number of circular holes, slits (notches), or rectangular holes, for example. The filter may have the same shape as the pipe, such as a cylindrical shape, but is not limited thereto.

When the filter is provided with circular holes, the diameter of each hole may be appropriately adjusted depending on the size of the crystals, and is preferably 50 to 500 μm, for example. The number of holes is not limited, and may be adjusted according to the pressure loss, for example.

The pipe that is connected to the filter and discharges a mother liquor is usually located above the filter.

The number of pipes that are connected to the filter and discharge a mother liquor is not limited. For example, in an industrial-scale hydraulic wash column, 50 to 350 pipes are preferably connected in parallel per square meter of the cross-sectional area of the hydraulic wash column.

The purification apparatus of the present invention may further include a mechanism that heats an outer wall surface of the hydraulic wash column.

Non-limiting examples of the mechanism that heats the outer wall surface of the hydraulic wash column include a heating medium, a steam tracing system, an electric tracing system, and a known heater that adjusts the environmental temperature of the column. For example, part of the hydraulic wash column may be heated with a heating medium or the like, and substantially the entire hydraulic wash column is preferably heated (jacket heating).

When the heating mechanism is of jacket heating, for example, the jacket may be made of any material such as metal (e.g., stainless steel or carbon steel) or resin.

The outside of the jacket may be provided with a heat insulating material, a tracing system, and the like.

The structure of the jacket is not limited.

The inside of the jacket may be provided with any structure such as a structure that promotes heat transfer, such as a baffle.

The jacket preferably has an average thickness (the width of the space where the heating medium flows) of 5 to 200 mm, for example.

The heat flux through the wall of the hydraulic wash column from the jacket is preferably more than 100 W/m$^2$, more preferably more than 200 W/m$^2$, still more preferably more than 500 W/m$^2$.

The upper limit of the heat flux through the wall of the hydraulic wash column from the jacket is usually 4000 W/m$^2$ or less, but is not limited thereto.

The difference between the melting point of the compound and the temperature of the heating medium fed to the jacket is preferably 1° C. or more, more preferably 2° C. or more, still more preferably 5° C. or more. The upper limit is usually 20° C., but is not limited thereto.

A side wall of the jacket may be provided with a sight glass (an observation window) or a hand hole (a hole for putting a hand inside during maintenance). In these cases, they can be covered with a cover. The numbers of sight glasses and hand holes to be provided are not limited.

Non-limiting examples of the heating medium include water, antifreeze, methanol water (an aqueous methanol solution), and gas. The heating medium may be appropriately selected in consideration of the freezing point of the compound to be purified, for example.

The number of pipes that feed the crystal-containing slurry to the hydraulic wash column and the number of feed nozzles (slurry feed ports) that may be connected to the tips of the pipes are not limited. Each of the numbers may be one or more (FIGS. 1 and 2 show the case where the number of pipes that feed the crystal-containing slurry to the hydraulic wash column is one).

The feed nozzle may have, at its tip, a distribution mechanism that distributes the slurry.

The hydraulic wash column may further include a distribution chamber and a central displacer body (see JP 2005-509010 T).

(Method for Producing Compound of the Present Invention)

The present invention also relates to a method for producing a compound, the method including: a step of feeding a slurry containing crystals of the compound to a hydraulic wash column; a step of melting crystals in a crystal-containing circulation slurry discharged from the hydraulic wash column; a step of returning a portion of a circulation liquid containing a melt obtained in the melting step to the hydraulic wash column; and a step of discharging a mother liquor, the step including filtering the crystal-containing slurry in the hydraulic wash column with a filter and discharging the mother liquor through a pipe connected to the filter, wherein a distance between a lower end of the filter and an average bottom surface level of the hydraulic wash column is 1000 mm or more.

In the method for producing a compound of the present invention, the distance between the lower end of the filter and the average bottom surface level of the hydraulic wash column is specified and/or the space velocity (SV) of the crystal bed below the filter in the hydraulic wash column may be specified.

For example, the present invention also relates to a method for producing a compound, the method including: a step of feeding a slurry containing crystals of the compound to a hydraulic wash column; a step of melting crystals in a crystal-containing circulation slurry discharged from the hydraulic wash column; a step of returning a portion of a circulation liquid containing a melt obtained in the melting step to the hydraulic wash column; and a step of discharging a mother liquor, the step including filtering the crystal-containing slurry in the hydraulic wash column with a filter and discharging the mother liquor through a pipe connected to the filter, wherein a crystal bed below the filter in the hydraulic wash column has a space velocity (1/h) of 1 or higher and 20 or lower.

The space velocity (1/h) of the crystal bed below the filter in the hydraulic wash column refers to the space velocity of the crystal bed during which the crystals at the height of the lower end of the filter are discharged through the discharging port for a crystal-containing circulation slurry of the hydraulic wash column. In other words, the space velocity (1/h) represents the flow rate ($m^3$/h) of crystals relative to the volume ($m^3$) from the lower end of the filter to the bottom surface of the hydraulic wash column in the hydraulic wash column.

For example, the space velocity (1/h) is calculated from the moving speed of the crystal bed measured through a sight glass provided on the side of the hydraulic wash column and the distance between the lower end of the filter and the average bottom surface level of the hydraulic wash column using the following formula (1).

Space velocity=Moving speed of crystal bed (mm/h)/Distance between lower end of filter of hydraulic wash column to average bottom surface level of column (mm) (1)

In the case of a substance whose weight ratio between the crystals and the mother liquor in the crystal bed is known, the space velocity is calculated by the following formula (2).

Space velocity=Crystal feed/Proportion by weight of crystals in crystal bed/(Crystal density×Proportion by weight of crystals in crystal bed+Mother liquor density×(1−Proportion by weight of crystals in crystal bed))/Volume from lower end of filter in hydraulic wash column to bottom surface of column (2)

The following describes the units of the parameters in the formula (2).

Crystal feed (t/h)

Proportion by weight of crystals in crystal bed (no unit)

Crystal density (t/$m^3$)

Mother liquor density (t/$m^3$)

Volume from lower end of filter in hydraulic wash column to bottom surface of column ($m^3$)

The proportion by weight of crystals in crystal bed refers to the ratio of the weight of the crystals in the slurry to the weight of the slurry, with the weight of the slurry taken as 1. The crystal bed is in a crystal-rich state, unlike the slurry fed to the hydraulic wash column (feed slurry). The crystal density is the density of the crystals themselves.

The space velocity (1/h) is more preferably 12 or lower, still more preferably 8 or lower, particularly preferably 6 or lower.

The space velocity (1/h) is more preferably 1.25 or higher, still more preferably 1.5 or higher.

In the method for producing a compound of the present invention, the ratio of the weight of the mother liquor to the weight of the crystals in the crystal-containing slurry fed to the hydraulic wash column per unit time is preferably 1 or more, more preferably 1.5 or more, still more preferably 2.3 or more, particularly preferably 4 or more.

The ratio of the weight of the mother liquor to the weight of the crystals in the crystal-containing slurry fed to the hydraulic wash column per unit time is preferably 99 or less, more preferably 32 or less, still more preferably 19 or less.

For example, in the method for producing a compound of the present invention, the ratio of the weight of the mother liquor to the weight of the crystals in the crystal-containing slurry fed to the hydraulic wash column per unit time is preferably 4 or more and 19 or less.

When the ratio of the weight of the mother liquor to the weight of the crystals is 4 or more, the amount of the mother liquor passing through the crystal bed deposited in the upper part of the filter increases, the ratio of the crystals to the crystal bed increases, and the mother liquor containing impurities is easily removed, further increasing the washing efficiency. Further, when the ratio is 19 or less, the mass of the mother liquor relative to the crystal feed per unit time is small, a compact pump can be used, the pressure in the apparatus is low, and higher pressure resistance of the apparatus is not required. The weight ratio of the crystals to the crystal bed is about 50% to 85%.

Herein, the crystal-containing slurry fed to the hydraulic wash column per unit time refers to the entire crystal-containing slurry fed to the hydraulic wash column in a unit time (1 h).

When a portion of the mother liquor discharged from the hydraulic wash column is recycled to the hydraulic wash column, the weight of this mother liquor is included in the weight of the mother liquor in the crystal-containing slurry fed to the hydraulic wash column per unit time.

In the method for producing a compound of the present invention, basically, an object to be purified is subjected to the feeding step, the melting step, and the returning step in this order. For example, as shown in FIG. 1, the crystal-containing slurry 11*a* is fed into the hydraulic wash column 1 through the feed line 11 and the pipe 4; a crystal-containing circulation slurry is discharged through the circulation slurry discharging port 20 at the bottom of the hydraulic wash column 1 and passes through the discharging line 21 that connects the circulation slurry discharging port 20 and the melting unit 22; and the crystals in the circulation slurry are melted in the unit 22. A portion of a circulation liquid containing the melt obtained by melting the crystals in the melting unit 22 is returned into the hydraulic wash column 1 through the return line 24 that connects the melting unit 22 and the return port 25. The rest of the circulation liquid passes through the product discharging line 23 branched from the return line 24 and is discharged from the purification apparatus as the product 23*a*. The following describes the feeding step, the melting step, and the returning step, followed by descriptions of the mother liquor discharging step and other steps. In a continuous purification process, the steps are usually performed simultaneously in the view of the whole purification apparatus.

Herein, the term "compound" refers to a compound obtained by the production method of the present invention, and does not refer to raw materials, by-products, and solvents in the production method of the present invention. The term "compound" may also be referred to as a "target compound" or a "target object". Herein, the term "impurity/impurities" refers to components other than the "compound", such as raw materials, by-products, and solvents.

<Feeding Step>

In the feeding step, the slurry containing crystals of the compound is fed to the hydraulic wash column. The crystal-containing slurry is a suspension of crystals of the compound and a mother liquor. In other words, the liquid portion of the slurry containing crystals of the compound to be fed to the hydraulic wash column is the mother liquor. The crystal-containing slurry can be obtained by generating crystals in a compound-containing solution (e.g., a (meth) acrylic acid aqueous solution or a crude (meth)acrylic acid solution) as described later. The compound-containing solution may be prepared in-house or procured from outside sources. The compound-containing solution encompasses a crude compound.

The mass percentage of the crystals in the crystal-containing slurry to be fed to the hydraulic wash column is preferably 1% by mass or more, more preferably 3% by mass or more, still more preferably 5% by mass or more.

The mass percentage of the crystals is preferably 50% by mass or less, more preferably 40% by mass or less, still more preferably 30% by mass or less, particularly preferably 20% by mass or less.

Herein, the expression "crystal-containing slurry to be fed to the hydraulic wash column" refers to the crystal-containing slurry immediately before being fed to the hydraulic wash column, and for example, refers to a crystal-containing slurry in a pipe that feeds a crystal-containing slurry to the hydraulic wash column.

Preferably, in the crystal-containing slurry to be fed to the hydraulic wash column, the mother liquor contains the compound. Examples of the mother liquor include the above-described compound and an aqueous solution of the compound. The mother liquor usually contains impurities other than the compound and water.

In the method for producing a compound of the present invention, the purity (mass percentage) of the compound in the mother liquor in the crystal-containing slurry to be fed to the hydraulic wash column is preferably 99% by mass or less. Thereby, the effect of the present invention can be significantly achieved.

The mass percentage of the compound in the mother liquor is more preferably 98% by mass or less, still more preferably 97% by mass or less, particularly preferably 96% by mass or less.

The mass percentage of the compound in the mother liquor is preferably 85% by mass or more, more preferably 88% by mass or more, still more preferably 90% by mass or more.

In the production method of the present invention, the compound preferably has a melting point of 0° C. to 80° C., more preferably 1° C. to 50° C., still more preferably 3° C. to 40° C., particularly preferably 5° C. to 20° C.

The compound having a melting point within the above range is preferably an easily polymerizable compound having a reactive double bond.

In particular, in the production method of the present invention, the compound is more preferably an unsaturated carboxylic acid, still more preferably (meth)acrylic acid, particularly preferably acrylic acid. Herein, the term "(meth) acrylic acid" refers to acrylic acid and/or methacrylic acid.

The mass percentage of water in the mother liquor is preferably 0.1% by mass or more, more preferably 0.5% by mass or more, still more preferably 1% by mass or more. The mass percentage of water in the mother liquor is preferably 8% by mass or less, more preferably 6% by mass or less, still more preferably 4% by mass or less.

The mass percentage of impurities other than the compound and water in the mother liquor is preferably 0.1% by mass or more, more preferably 0.4% by mass or more, still more preferably 0.8% by mass or more, in order to make the effect of the invention significant.

The mass percentage of impurities other than the compound and water in the mother liquor is preferably 8% by mass or less, more preferably 6% by mass or less, still more preferably 4% by mass or less.

When the compound is (meth)acrylic acid, the impurities other than the compound and water may include acetic acid and furfural, for example.

In this case, the mass percentage of acetic acid in the mother liquor is preferably 0.1% by mass or more, more preferably 0.3% by mass or more, still more preferably 0.7% by mass or more, in order to make the effect of the invention significant.

The mass percentage of acetic acid in the mother liquor is preferably 8% by mass or less, more preferably 6% by mass or less, still more preferably 4% by mass or less.

When the compound is (meth)acrylic acid, the mass percentage of furfural in the mother liquor is more preferably 0.01% by mass or more, more preferably 0.05% by mass or more, still more preferably 0.1% by mass or more, in order to make the effect of the invention significant.

The mass percentage of furfural in the mother liquor is preferably 2% by mass or less, more preferably 1% by mass or less, still more preferably 0.5% by mass or less.

In the feeding step, the crystal-containing slurry may be fed at any feed rate. The feed rate is, for example, $0.2\times10^3$ to $4.0\times10^5$ kg/h in an industrial-scale hydraulic wash column.

In the feeding step, the feed temperature of the crystal-containing slurry can be appropriately selected according to the melting point of the compound or the like. For example, the feed temperature can be appropriately adjusted within the range of 0° C. to 80° C.

For example, when the compound is (meth)acrylic acid, the feed temperature of the crystal-containing slurry is preferably 5° C. to 13° C., more preferably 6° C. to 12° C.

The feed temperature of the crystal-containing slurry is the temperature of the mother liquor in the crystal-containing slurry immediately before being fed to the hydraulic wash column.

<Melting Step>

In the melting step, the crystals in the crystal-containing circulation slurry discharged from the hydraulic wash column are melted.

The crystals originate from a crystal bed formed at the bottom of the hydraulic wash column. The crystals can be discharged using the above-described mechanism that discharges the crystals from the crystal bed in the hydraulic wash column.

The crystals are usually discharged together with the circulation liquid, i.e., the crystals are discharged in the form of a crystal-containing circulation slurry. This circulation slurry is subjected to the melting step.

The circulation liquid is circulated as follows: the circulation liquid is discharged in the form of crystal-containing circulation slurry from the hydraulic wash column; and a portion of the circulation liquid containing the melt obtained in the melting step is returned to the hydraulic wash column and passes through the hydraulic wash column for circulation. In other words, the circulation liquid flows through a circulation path that passes through the hydraulic wash column for circulation. Herein, the liquid component in the circulation slurry flowing through the circulation path is also referred to as a circulation liquid.

Here, the circulation slurry is a suspension of crystals of the compound and the circulation liquid, and flows through the circulation path.

For example, the mass percentage of the crystals in the crystal-containing circulation slurry discharged from the hydraulic wash column is preferably 0.5% by mass or more, more preferably 1% by mass or more, still more preferably 3% by mass or more, particularly preferably 5% by mass or more.

The mass percentage of the crystals is preferably 40% by mass or less, more preferably 30% by mass or less, still more preferably 20% by mass or less, particularly preferably 10% by mass or less.

Herein, the crystal-containing circulation slurry discharged from the hydraulic wash column refers to the crystal-containing circulation slurry immediately after being discharged from the hydraulic wash column, and, for example, refers to the crystal-containing circulation slurry in the discharging line (pipe) that connects the circulation slurry discharging port and the melting unit.

The crystal-containing circulation slurry is discharged from the hydraulic wash column at a discharging rate of $2\times10^3$ to $5\times10^5$ kg/h in an industrial-scale hydraulic wash column, for example, but is not limited thereto.

The discharged crystals can be melted using a heater. Examples of the heater include those having a structure that efficiently transfers heat to the crystal-containing slurry, such as a vertical multitubular heat exchanger, a horizontal multitubular heat exchanger, a double pipe heat exchanger, a spiral heat exchanger, a plate heat exchanger, a corrugated tube heat exchanger, or an electric heater. Preferably, the heater is provided in the melt loop and the circulation slurry (the circulation liquid after the melting step) is circulated in the forced circulation system in which the circulation slurry is circulated by a pump provided in the melt loop.

The heating temperature in the melting step may be appropriately selected according to the melting point of the compound, and can be adjusted within the range of 10° C. to 100° C., for example.

For example, when the compound is (meth)acrylic acid, the heating temperature in the melting step is preferably 15° C. or higher, more preferably 18° C. or higher. The heating temperature is preferably 50° C. or lower, more preferably 40° C. or lower.

When the heating is performed by feeding a heating medium to the melting unit, the heating temperature in the melting step is the feed temperature of the heating medium.

The temperature of the circulation liquid containing the melt at the outlet of the melting step (the melting unit) is preferably set to a temperature 1° C. to 10° C. higher than the melting point of the circulation liquid containing the melt obtained in the melting step (e.g., the circulation liquid containing the melt obtained after the crystal-containing slurry passes through the heat exchanger or the like and the crystals are melted).

The melting time in the melting step may be appropriately selected to the extent that the crystals are sufficiently melted.

In the production method of the present invention, the melting step is carried out using a unit that melts crystals. In the melting unit, the linear velocity of the circulation slurry or the circulation liquid containing a melt is preferably 0.05 to 4 m/s.

More preferably, the linear velocity is 0.1 m/s or higher. This results in better heat transfer performance in the melting unit. In other words, with higher linear velocity, the circulation slurry or the circulation liquid containing a melt is better mixed, and the heat transfer surface is renewed, resulting in acceleration of heat transfer.

The linear velocity is more preferably 3 m/s or lower, still more preferably 2 m/s or lower. A linear velocity within such a range can prevent an increase in the pressure loss in the melting unit, which is caused when the linear velocity is too high, thereby enabling stable operation.

The linear velocity can be determined as follows: the volume flow rate of the circulation slurry or the circulation liquid containing a melt in the melting unit is measured with a flow meter, and the volume flow rate is divided by the cross-sectional area of the heat exchange part, in the melting unit, through which the circulation slurry or the circulation liquid containing a melt flows. When the linear velocity changes in the melting unit, the average linear velocity corresponding to the ratio of the heat transfer area may be used for the determination.

<Returning Step>

The returning step includes returning a portion of a circulation liquid containing a melt obtained in the melting step to the hydraulic wash column.

The circulation liquid contains the melt obtained in the melting step. In other words, the crystals in the discharged circulation slurry are melted to be a melt, so that the suspended circulation slurry becomes a non-suspended circulation liquid.

The melt obtained in the melting step refers to a liquid obtained by melting the crystals in the circulation slurry discharged from the hydraulic wash column in the melting step. The melt does not include those derived from the circulation liquid (liquid components) in the circulation slurry.

A portion of the circulation liquid containing the melt obtained in the melting step is returned to the hydraulic wash column, and a portion of the returned circulation liquid is used as a washing liquid for crystals in the hydraulic wash column.

The washing liquid is a portion of the circulation liquid that is returned to the hydraulic wash column. After returning to the hydraulic wash column, the portion of the circulation liquid is not discharged through the discharging port of the hydraulic wash column and is not recirculated in the circulation path, but, for example, flows countercurrent (preferably in an upward direction) to the conveying direction of the crystals through gaps between crystals of a crystal bed in the hydraulic wash column, thereby washing the crystals in the hydraulic wash column.

When a portion of the circulation liquid is returned to the hydraulic wash column in the returning step, the portion of the circulation liquid is preferably returned such that it flows countercurrent to the conveying direction of the crystals (bed). The direction may be appropriately determined depending on the densities of the washing liquid and the crystals. For example, when the density of the crystals is greater than the density of the mother liquor, the circulation liquid is preferably returned such that it flows in an upward direction. The term "upward direction" preferably refers to a substantially vertically upward direction with respect to the horizontal plane. Thus, the crystals can be washed efficiently.

The return percentage in the returning step is preferably 1% by mass or more and 80% by mass or less, but is not limited thereto. Herein, the return percentage refers to a percentage by mass of the washing liquid for crystals relative to 100% by mass of the melt. The melt is contained in the circulation liquid and thus cannot be separated as the melt.

In other words, preferably, the returning step includes returning a portion of the circulation liquid containing a melt to the hydraulic wash column, wherein the circulation liquid returned in the returning step in an amount of 1% by mass or more and 80% by mass or less relative to 100% by mass of the melt serves as a washing liquid for crystals.

As described above, the washing liquid is a portion that is not recirculated in the circulation path, but is separated from the circulation liquid flowing in the circulation path after the circulation liquid is returned to the hydraulic wash column. A product is also discharged to be separated from the circulation liquid flowing in the circulation path. Separately, the crystals are discharged from the hydraulic wash column and introduced into the circulation liquid flowing in the circulation path. The amount removed from the circulation path and the amount introduced into the circulation path are balanced during continuous operation. The sum of the amount of the washing liquid and the amount of the product discharged is equal to the amount of the crystals discharged from the hydraulic wash column, i.e., the amount of the melt obtained in the melting step. This also indicates that the amount of the washing liquid is equal to the amount obtained by subtracting the amount of the discharged product from the amount of the melt of the discharged crystals.

The return percentage in the returning step can be determined as follows: the amount of the crystals fed to the melting step is determined in terms of the flow rate of the slurry fed to the hydraulic wash column and the concentration of the slurry determined from sampling, density measurement, the freezing point of the mother liquor, and the like, and the flow rate of the circulation liquid discharged as a product is measured with a flow meter. Alternatively, the return percentage can be determined from the impurity concentration in the mother liquor in the slurry fed to the hydraulic wash column (hereinafter also referred to as a feed slurry), the impurity concentration in the discharged mother liquor, and the impurity concentration in the discharged product.

In an industrial-scale hydraulic wash column, in discharging a product accompanying the returning step, the product is discharged at a rate of 5 kg/h to $4.0\times10^4$ kg/h.

In the production method of the present invention, the outer wall surface of the hydraulic wash column may be heated by a heating medium or the like, and the temperature of the heating medium used for heating is appropriately set according to a substance to be treated, that is, a target compound.

The heating medium may be any liquid or gas, and examples include water, antifreeze, methanol water (aqueous methanol solution), and gas. The heating medium may be appropriately selected in consideration of the freezing point of the compound to be purified and the like.

Such freezing can be prevented by heating the outer wall surface of the hydraulic wash column, leading to stable production of the compound.

The heating may be performed by heating part of the hydraulic wash column with a heating medium or the like. Preferably, substantially the entire hydraulic wash column is heated (jacket heating).

During operation, the inside of the hydraulic wash column is basically under pressure. The pressure is preferably within the range of 0.05 to 1.0 MPa.

<Mother Liquor Discharging Step>

The production method of the present invention includes a step of discharging a mother liquor, the step including filtering the crystal-containing slurry in the hydraulic wash column with a filter and discharging the mother liquor through a pipe connected to the filter. In the mother liquor discharging step, a portion of the washing liquid is discharged together with the mother liquor. Thus, the discharged mother liquor contains a portion of the washing liquid.

The discharged mother liquor can be recycled and reused. For example, reuse of the discharged mother liquor at least as a portion of the crystal-containing slurry to be fed to the hydraulic wash column can provide a compound with further improved quality.

When the density of the crystals is higher than that of the mother liquor, the mother liquor in the slurry fed in the feeding step flows downward from the top, runs into the washing liquid flowing upward from the bottom, and is pushed back. Thereby, the mother liquor is discharged through the filter.

The filter may be made of any material and may be made of, for example, metal such as stainless steel or resin such as polytetrafluoroethylene (PTFE) or polyetheretherketone (PEEK), with the latter being preferred. The pipe may be made of any material and is preferably made of metal or an alloy.

The mother liquor discharged in the mother liquor discharging step usually contains the compound. Examples of the mother liquor include a melt of the compound and an aqueous solution of the compound. The mother liquor usually contains impurities other than the compound and water.

The mother liquor discharged in the mother liquor discharging step refers to the mother liquor immediately after passing through the filter in the mother liquor discharging step.

The mother liquor discharging step can be appropriately performed using a pump or the like.

<Mixing Step>

The production method of the present invention preferably further includes a step of mixing a portion of the circulation liquid containing the melt obtained in the melting step with the circulation slurry discharged from the hydraulic wash column without returning the portion of the circulation liquid to the hydraulic wash column.

In other words, the production method of the present invention preferably includes a step of returning a first portion of the circulation liquid containing the melt obtained in the melting step to the hydraulic wash column, and a step of mixing a second portion of the circulation liquid with the circulation slurry discharged from the hydraulic wash column before the melting step without returning the second portion of the circulation liquid to the hydraulic wash column.

In the production method of the present invention, the mass ratio of the circulation liquid returned to the hydraulic wash column in the returning step to the circulation liquid mixed with the circulation slurry in the mixing step is preferably 1:0.01 to 1:4.

The mass ratio is more preferably 1:0.1 to 1:3, still more preferably 1:0.3 to 1:2.

The mass ratio can be determined, for example, by directly measuring the flow rate of the circulation liquid containing the melt obtained in the melting step in the bypass line and the flow rate of the circulation liquid containing the melt obtained in the melting step returned to the hydraulic wash column with flow meters or the like. The flow rate in the bypass line refers to the flow rate of a bypass liquid immediately before mixing with the circulation slurry, and the flow rate of the circulation liquid returned to the hydraulic wash column refers to the flow rate of the circulation liquid immediately before returning to the hydraulic wash column.

<Step of Preparing Crystal-Containing Slurry>

The production method of the present invention preferably further includes a step of preparing a slurry containing crystals of a compound from a compound-containing solution.

The compound-containing solution can be prepared by collecting the gas of a compound, which is a reaction product obtained by a reactor, in an absorption tower, for example. The compound-containing solution encompasses a crude compound obtained by purifying the collected compound. The compound-containing solution is not limited to one synthesized in-house, and may be one procured from outside sources.

The compound-containing solution is cooled, for example, and thereby the slurry containing crystals of the compound can be obtained.

The compound-containing solution contains impurities other than the compound and water.

In the production method of the present invention, the compound-containing solution is preferably a (meth)acrylic acid aqueous solution or a crude (meth)acrylic acid solution.

The (meth)acrylic acid aqueous solution refers to a solution in which (meth)acrylic acid is dissolved in water. The crude (meth)acrylic acid solution is a solution composed of (meth)acrylic acid and containing impurities such as by-products produced during the production of the (meth) acrylic acid.

Examples of the impurities include acids such as propionic acid, acetic acid, maleic acid, benzoic acid, and acrylic acid dimers; aldehydes such as acrolein, furfural, formaldehyde, and glyoxal; acetone; methyl isobutyl ketone; toluene; and protoanemonin.

The production method of the present invention can sufficiently remove the impurities in the compound-containing solution.

<Step of Preparing Compound-Containing Solution>

The production method of the present invention preferably further includes a step of preparing the compound-containing solution from a raw material.

The step of preparing the compound-containing solution may be any step that can provide the compound-containing solution. When the compound is (meth)acrylic acid, the step can be suitably carried out by synthesizing acrylic acid, collecting the acrylic acid, and the like, as described in JP 2007-182437 A (Patent Literature 1), for example.

In the method for producing a compound of the present invention, the raw material is at least one selected from the group consisting of propane, propylene, acrolein, isobutene, methacrolein, acetic acid, lactic acid, isopropanol, 1,3-propanediol, glycerol, and 3-hydroxypropionic acid, and the compound-containing solution is preferably a (meth)acrylic acid aqueous solution or a crude (meth)acrylic acid solution. The (meth)acrylic acid and/or the raw material may also be bio-based (meth)acrylic acids derived from renewable raw materials.

In the step of preparing the compound-containing solution, impurities such as by-products are basically generated. For example, when the compound is (meth)acrylic acid, the impurities generated include water; acids such as propionic acid, acetic acid, maleic acid, benzoic acid, and acrylic acid dimers; aldehydes such as acrolein, furfural, formaldehyde, and glyoxal; acetone; methyl isobutyl ketone; toluene; and protoanemonin. Such impurities can be efficiently separated by purification using the hydraulic wash column in the production method of the present invention. Thereby, a product can be efficiently obtained.

(Method for Purifying Compound)

The present invention also relates to a method for purifying a compound, the method including: a step of feeding a slurry containing crystals of the compound to a hydraulic wash column; a step of melting crystals in a crystal-containing circulation slurry discharged from the hydraulic wash column; a step of returning a portion of a circulation liquid containing a melt obtained in the melting step to the hydraulic wash column; and a step of discharging a mother liquor, the step including filtering the crystal-containing slurry in the hydraulic wash column with a filter and discharging the mother liquor through a pipe connected to the filter, wherein a distance between a lower end of the filter and an average bottom surface level of the hydraulic wash column is 1000 mm or more.

The present invention also relates to a method for purifying a compound, the method including: a step of feeding a slurry containing crystals of the compound to a hydraulic wash column; a step of melting crystals in a crystal-containing circulation slurry discharged from the hydraulic wash column; a step of returning a portion of a circulation liquid containing a melt obtained in the melting step to the hydraulic wash column; and a step of discharging a mother liquor, the step including filtering the crystal-containing slurry in the hydraulic wash column with a filter and discharging the mother liquor through a pipe connected to the filter, wherein a crystal bed below the filter in the hydraulic wash column has a space velocity (1/h) of 1 or higher and 20 or lower.

In the method for purifying a compound of the present invention, the ratio of the weight of the mother liquor to the weight of the crystals in the crystal-containing slurry to be fed to the hydraulic wash column per unit time is preferably 1 or more and 99 or less.

The purification method of the present invention preferably further includes a step of mixing a portion of the circulation liquid containing the melt obtained in the melting step with the circulation slurry discharged from the hydraulic wash column without returning the portion of the circulation liquid to the hydraulic wash column.

In other words, the purification method of the present invention preferably includes a step of returning a first portion of the circulation liquid containing the melt obtained in the melting step to the hydraulic wash column, and a step of mixing a second portion of the circulation liquid with the circulation slurry discharged from the hydraulic wash column before the melting step without returning the second portion of the circulation liquid to the hydraulic wash column.

The purification method of the present invention can efficiently purify the crystal-containing slurry.

Preferred embodiments of the purification method of the present invention are the same as the preferred embodiments of the production method of the present invention described above.

EXAMPLES

The present invention will be described in more detail below with reference to examples, but the present invention is not limited by the following examples, and appropriate modifications may be made within the scope that can conform to the gist of the above and later descriptions. All of them are included in the technical scope of the present invention.

Unless otherwise specified, "%" indicates "% by mass" and "parts" indicates "parts by mass."

<Measurement of Space Velocity of Crystal Bed>

The space velocity was calculated by the formula (1) using the moving speed of the crystal bed visually observed and measured.

(Measurement Instruments for Gas Chromatography and Liquid Chromatography)

Gas chromatograph: GC-2014 available from Shimadzu Corporation

Liquid chromatograph: LC-20AD HPLC unit available from Shimadzu Corporation

These instruments were used for measurement of acetic acid and furfural.

(Method for Preparing Acrylic Acid Aqueous Solution)

An acrylic acid aqueous solution was prepared according to the method described in WO 2010/032665 as follows: propylene was catalytically oxidized in gas phase to obtain an acrylic acid-containing gas; and the acrylic acid-containing gas was treated in an absorption tower.

(Method for Preparing Feed Slurry)

The acrylic acid aqueous solution was fed to a crystallization vessel having a capacity of 5 L and a heat transfer area of 0.14 $m^2$. A cooling medium was fed to a jacket provided around the wall of the crystallization vessel for indirect cooling. Crystals adhering to the inner surface of the crystallization vessel were scraped off with a scraper attached in the crystallization vessel. Thus, a crystal-containing slurry (feed slurry) was prepared.

The concentrations of acrylic acid, acetic acid, and furfural in the mother liquor in the feed slurry were 94% by mass, 1.5% by mass, and 1500 ppm, respectively.

Examples 1 to 3, Comparative Examples 1 and 2

(Purification Apparatus)

A purification apparatus used includes the following units and is similar to the purification apparatus shown in FIG. 1, except for the number of filters 2 and the number of mother liquor discharging pipes 3.

Hydraulic wash column 1: inner diameter 40 mm; height 3000 mm

Filter 2: inner diameter 10 mm; length (height) 50 mm; number of filters 1; structure of filter: circular holes with a diameter of 250 μm Pipe 3 that is connected to the filter 2 and discharges a mother liquor: inner diameter 10 mm; number of pipes 1

Return of circulation liquid into the hydraulic wash column 1: upward return from the bottom of the column through the return port 25

Melting unit 22: corrugated tube heat exchanger

Distance 31 between the lower end of the filter and the bottom surface of the column: 1000 mm Space velocity of the crystal bed below the filter: 6 (1/h)

The line between the discharging port 20 and the return port 25 was heated with a water jacket.

(Method for Operating Purification Apparatus)

The purification apparatus was operated in the following way.

A slurry containing acrylic acid crystals (feed slurry) was fed to the hydraulic wash column prepared as above under the conditions of a slurry concentration (crystal concentration) of 10% by mass, a slurry temperature of 9° C., and a crystal feed of 8.4 kg/h.

The exterior environment of the hydraulic wash column was held at 25° C.

The crystals were discharged together with the circulation liquid through the discharging port 20 of the hydraulic wash column 1 and were sent as a circulation slurry to a corrugated tube heat exchanger, which was a melting unit, at a flow rate of 84 kg/h. The linear velocity of the circulation slurry or the circulation liquid containing a melt in the corrugated tube heat exchanger was 0.07 m/s.

When the temperature of water fed to the corrugated tube heat exchanger was adjusted so that the temperature of the circulation liquid at the outlet of the corrugated tube heat exchanger was 18° C., the temperature of water was 35° C.

While a portion of the circulation liquid was discharged at 5.9 kg/h as a product through the product discharging line 23, the rest of the circulation liquid was returned to the hydraulic wash column.

(Measurement of Impurities)

A liquid product sample was subjected to high-performance liquid chromatography and gas chromatography, and the concentrations of acetic acid and furfural as impurities in the product were measured. Table 1 shows the results.

Example 1

Acrylic acid was obtained as a product using the purification apparatus and its operation method described above. Table 1 shows the concentrations of acetic acid and furfural in the product.

Example 2, Comparative Example 1

Acrylic acid was obtained as a product as in Example 1, except that the distance between the lower end of the filter and the bottom surface of the column and the space velocity of the crystal bed below the filter were changed as shown in Table 1. Table 1 shows the concentrations of acetic acid and furfural in the product.

Example 3, Comparative Example 2

Acrylic acid was obtained as a product as in Example 1, except that the distance between the lower end of the filter and the bottom surface of the column and the space velocity of the crystal bed below the filter were changed as shown in Table 1 and that the crystal concentration of the slurry containing acrylic acid crystals fed to the hydraulic wash column was 25%. Table 1 shows the concentrations of acetic acid and furfural in the product.

TABLE 1

| | Distance (mm) between lower end of filter and bottom surface of column | Space velocity (1/h) of crystal bed below filter | Concentration in product (ppm) | | Weight ratio of mother liquor to crystals in feed slurry |
|---|---|---|---|---|---|
| | | | Acetic acid | Furfural | |
| Example 1 | 1000 | 6 | 1360 | 0.4 | 9 |
| Example 2 | 2000 | 3 | 940 | 0.3 | 9 |
| Comparative Example 1 | 200 | 30 | 2140 | 0.8 | 9 |
| Example 3 | 1000 | 6.1 | 1600 | 4.0 | 3 |
| Comparative Example 2 | 200 | 30.5 | 2600 | 7.0 | 3 |
| Example 4 | 500 | 6 | 1350 | 0.4 | 9 |

The results of Examples 1 to 3 and Comparative Examples 1 and 2 in Table 1 demonstrated that excellent impurity separation efficiency can be achieved and a product can be efficiently obtained by a method for producing a compound including: a step of feeding a slurry containing crystals of the compound to a hydraulic wash column; a step of melting crystals in a crystal-containing circulation slurry discharged from the hydraulic wash column; a step of returning a portion of a circulation liquid containing a melt obtained in the melting step to the hydraulic wash column; and a step of discharging a mother liquor, the step including filtering the crystal-containing slurry in the hydraulic wash column with a filter and discharging the mother liquor through a pipe connected to the filter, wherein a distance between a lower end of the filter and an average bottom surface level of the hydraulic wash column is 1000 mm or more.

A distance between the lower end of the filter and the average bottom surface level of the hydraulic wash column of 1000 mm or more appropriately reduced the space velocity of the crystal bed below the filter in the hydraulic wash column. In other words, it is considered that the residence time of the crystal bed below the filter is sufficiently long, leading to excellent impurity separation efficiency.

Therefore, even a larger one of the purification apparatus of the present invention can achieve the effects of the present invention, i.e., providing high-quality products, as long as the distance between the lower end of the filter and the average bottom surface level of the hydraulic wash column is 1000 mm or more.

Example 4

Acrylic acid was obtained as a product as in Example 1, except that the crystal feed to the hydraulic wash column was changed to 4.2 kg/h, the product was discharged at a flow rate of 2.9 kg/h, and the distance between the lower end of the filter and the bottom surface of the column was changed to 500 mm. Table 1 shows the concentrations of acetic acid and furfural in the product.

The results of Example 4 demonstrated that even when the distance between the lower end of the filter and the average bottom surface level of the hydraulic wash column is less than 1000 mm, excellent impurity separation efficiency can be achieved and a product can be efficiently obtained by an appropriate space velocity of the crystal bed below the filter in the hydraulic wash column.

Example 5

The same purification apparatus as in Example 1 was operated under the same conditions as in Example 1, except that a bypass line that connected the discharging line and the return line was provided. In other words, the purification apparatus used included the following units and was similar to the purification apparatus shown in FIG. 2, except for the number of filters 102 and the number of mother liquor discharging pipes 103 and that the bypass line was provided with no valve V, and the purification apparatus was operated under the same conditions as in Example 1.

Hydraulic wash column 101: inner diameter 40 mm; height 3000 mm

Filter 102: inner diameter 10 mm; length (height) 50 mm; number of filters 1; structure of filter: circular holes with a diameter of 250 μm Pipe 103 that is connected to the filter 102 and discharges a mother liquor: inner diameter 10 mm; number of pipes 1

Return of circulation liquid into the hydraulic wash column 101: upward return from the bottom of the column through a return port 125

Melting unit 122: corrugated tube heat exchanger

Distance 131 between the lower end of the filter and the bottom surface of the column: 1000 mm Space velocity of the crystal bed below the filter: 6 (1/h)

The following describes the flow rate in the bypass line 126, and the flow rate and linear velocity of the circulation slurry or the circulation liquid containing a melt, flowing through the corrugated tube heat exchanger for operation.

Flow rate in the bypass line 126: 84 kg/h

Flow rate of the circulation slurry or the circulation liquid containing a melt, flowing through the corrugated tube heat exchanger: 168 kg/h Linear velocity of the circulation slurry or the circulation liquid containing a melt, flowing through the corrugated tube heat exchanger: 0.14 m/s As in Example 1, when the temperature of water fed to the corrugated tube heat exchanger was adjusted so that the temperature of the circulation liquid at the outlet of the corrugated tube heat exchanger was 18° C., the temperature of water was 32° C.

The presence of the bypass line 126 improved the heat exchange efficiency of the corrugated tube heat exchanger and allowed the crystals in the circulation slurry to be melted at a lower set temperature.

Since the set temperature of the melting unit can be reduced, polymerization can be suppressed, stable operation can be achieved, and a product can be produced more efficiently in treatment of easily polymerizable substances such as (meth)acrylic acid. The concentrations of acetic acid and furfural in acrylic acid obtained as a product were the same as those in Example 1.

REFERENCE SIGNS LIST

- 1, 101 hydraulic wash column
- 2, 102 filter that filters crystal-containing slurry in hydraulic wash column
- 3, 103 pipe that is connected to filter and discharges mother liquor
- 4, 104 pipe that feeds crystal-containing slurry to hydraulic wash column
- 11, 111 feed line (that feeds crystal-containing slurry to hydraulic wash column)
- 11*a*, 111*a* crystal-containing slurry
- 12, 112 mother liquor
- 20, 120 circulation slurry discharging port
- 21, 121 discharging line that connects circulation slurry discharging port and melting unit
- 22, 122 melting unit
- 23, 123 product discharging line (connected to product discharging port)
- 23*a*, 123*a* (purified) product
- 24, 124 return line (that connects melting unit and return port)
- 121*a* portion that connects circulation slurry discharging port and junction of discharging line and bypass line
- 121*b* portion that connects junction of discharging line and bypass line and melting unit
- 124*a* portion that connects melting unit and branch where bypass line branches from return line
- 124*b* portion that connects return port and branch where bypass line branches from return line
- 25, 125 return port (for circulation liquid containing melt of discharged crystals)

31, 131 distance between lower end of filter and bottom surface of column

126 bypass line

P pump

V valve

The invention claimed is:

1. A purification apparatus that purifies crystals, the purification apparatus comprising:

a hydraulic wash column that includes a discharging port for a crystal-containing circulation slurry and a return port for a circulation liquid containing a melt of discharged crystals;

a pipe that feeds a crystal-containing slurry to the hydraulic wash column;

a filter that filters the crystal-containing slurry in the hydraulic wash column;

a pipe that is connected to the filter and discharges a mother liquor; and a unit that melts crystals in a circulation slurry discharged through the discharging port, wherein a distance between a lower end of the filter and an average bottom surface level of the hydraulic wash column is 1000 mm or more.

2. The purification apparatus according to claim 1, wherein the distance between the lower end of the filter and the average bottom surface level of the hydraulic wash column is 10000 mm or less.

3. The purification apparatus according to claim 1, further comprising:

a discharging line that connects the discharging port and the melting unit;

a return line that connects the melting unit and the return port; and a bypass line that connects the discharging line and the return line.

4. A method for producing a compound, the method comprising:

a step of feeding a slurry containing crystals of the compound to a hydraulic wash column;

a step of melting crystals in a crystal-containing circulation slurry discharged from the hydraulic wash column;

a step of returning a portion of a circulation liquid containing a melt obtained in the melting step to the hydraulic wash column; and a step of discharging a mother liquor, the step including filtering the crystal-containing slurry in the hydraulic wash column with a filter and discharging the mother liquor through a pipe connected to the filter, wherein a distance between a lower end of the filter and an average bottom surface level of the hydraulic wash column is 1000 mm or more.

5. The method for producing a compound according to claim 4, wherein a crystal bed below the filter in the hydraulic wash column has a space velocity (1/h) of 1 or higher and 20 or lower.

6. The method for producing a compound according to claim 4, wherein a ratio of a weight of the mother liquor to a weight of crystals in the crystal-containing slurry to be fed to the hydraulic wash column per unit time is 1 or more and 99 or less.

7. The method for producing a compound according to claim 4, further comprising a step of mixing a portion of the circulation liquid containing the melt obtained in the melting step with the circulation slurry discharged from the hydraulic wash column without returning the portion of the circulation liquid to the hydraulic wash column.

8. The method for producing a compound according to claim 4, further comprising a step of preparing the slurry containing crystals of the compound from a compound-containing solution.

9. The method for producing a compound according to claim 8, wherein the compound-containing solution is a (meth) acrylic acid aqueous solution or a crude (meth)acrylic acid solution.

10. The method for producing a compound according to claim 4, further comprising a step of preparing a compound-containing solution from a raw material.

11. The method for producing a compound according to claim 10, wherein the raw material is at least one selected from the group consisting of propane, propylene, acrolein, isobutene, methacrolein, acetic acid, lactic acid, isopropanol, 1,3-propanediol, glycerol, and 3-hydroxypropionic acid; and wherein the compound-containing solution is a (meth)acrylic acid aqueous solution or a crude (meth)acrylic acid solution.

12. A method for purifying a compound, the method comprising:

a step of feeding a slurry containing crystals of the compound to a hydraulic wash column;

a step of melting crystals in a crystal-containing circulation slurry discharged from the hydraulic wash column;

a step of returning a portion of a circulation liquid containing a melt obtained in the melting step to the hydraulic wash column; and a step of discharging a mother liquor, the step including filtering the crystal-containing slurry in the hydraulic wash column with a filter and discharging the mother liquor through a pipe connected to the filter, wherein a distance between a lower end of the filter and an average bottom surface level of the hydraulic wash column is 1000 mm or more.

13. The method for purifying a compound according to claim 12, wherein a crystal bed below the filter in the hydraulic wash column has a space velocity (1/h) of 1 or higher and 20 or lower.

14. The method for purifying a compound according to claim 12, wherein a ratio of a weight of the mother liquor to a weight of crystals in the crystal-containing slurry to be fed to the hydraulic wash column per unit time is 1 or more and 99 or less.

15. The method for purifying a compound according to claim 12, further comprising a step of mixing a portion of the circulation liquid containing the melt obtained in the melting step with the circulation slurry discharged from the hydraulic wash column without returning the portion of the circulation liquid to the hydraulic wash column.

16. The method for producing a compound according to claim 4, wherein a mass percentage of the crystals in the crystal-containing slurry to be fed to the hydraulic wash column is 1% by mass or more and 50% by mass or less.

17. The method for producing a compound according to claim 4, wherein a mass percentage of the compound in the mother liquor in the crystal-containing slurry to be fed to the hydraulic wash column is 85% by mass or more and 99% by mass or less.

18. The method for producing a compound according to claim 4, wherein the melting step is carried out using a unit that melts crystals, and in the melting unit, a linear velocity of the circulation slurry or the circulation liquid containing the melt is 0.05 to 4 m/s.

19. The method for producing a compound according to claim 4, wherein the circulation liquid returned in the returning step in an amount of 1% by mass or more and 80% by mass or less relative to 100% by mass of the melt serves as a washing liquid for crystals.

* * * * *